United States Patent
Lamberson et al.

(10) Patent No.: US 9,995,665 B2
(45) Date of Patent: Jun. 12, 2018

(54) DYNAMIC IMPACT FATIGUE DEVICE

(71) Applicants: Leslie Elise Lamberson, Philadelphia, PA (US); Steven J. Pagano, Philadelphia, PA (US); Peter A. Jewell, Delran, NJ (US)

(72) Inventors: Leslie Elise Lamberson, Philadelphia, PA (US); Steven J. Pagano, Philadelphia, PA (US); Peter A. Jewell, Delran, NJ (US)

(73) Assignee: Drexel University, Philadelphia, PA (US)

( * ) Notice: Subject to any disclaimer, the term of this patent is extended or adjusted under 35 U.S.C. 154(b) by 259 days.

(21) Appl. No.: 15/083,403

(22) Filed: Mar. 29, 2016

(65) Prior Publication Data

US 2016/0290904 A1    Oct. 6, 2016

Related U.S. Application Data

(60) Provisional application No. 62/142,500, filed on Apr. 3, 2015.

(51) Int. Cl.
| | |
|---|---|
| *G01N 3/30* | (2006.01) |
| *G01N 7/08* | (2006.01) |
| *G01N 3/38* | (2006.01) |
| *G01N 3/32* | (2006.01) |

(52) U.S. Cl.
CPC ............... *G01N 3/38* (2013.01); *G01N 3/32* (2013.01)

(58) Field of Classification Search
CPC  G01N 3/34; G01N 3/307; G01N 3/48; G01N 2203/0032; G01N 2203/0035; G01N 2203/005
See application file for complete search history.

(56) References Cited

U.S. PATENT DOCUMENTS

| | | | |
|---|---|---|---|
| 2,662,392 A | * | 12/1953 | Sullivan ................ G01N 3/303 73/12.06 |
| 3,177,386 A | | 4/1965 | Macchioni et al. |
| 3,371,770 A | * | 3/1968 | Graham ............. B28B 19/0038 198/572 |
| 3,374,662 A | | 3/1968 | Achter et al. |
| (Continued) | | | |

OTHER PUBLICATIONS

Title: Scientific Research; Date: Oct. 15, 2014; URL: http://file.scirp.org/Html/3-4900181_30860.htm.*

*Primary Examiner* — Leslie J Evanisko
*Assistant Examiner* — Ruben Parco, Jr.
(74) *Attorney, Agent, or Firm* — Joseph E. Maenner; Maenner & Associates, LLC

(57) ABSTRACT

An impact fatigue device includes a striker rod assembly configured to reciprocally move between an upstream position and a downstream position. The striker rod assembly includes a striker rod slidingly mounted on a support member and a trigger located upstream of the striker rod and adapted to move downstream to engage the striker rod and propel the striker rod downstream. An actuator assembly is located upstream of the striker rod assembly. The actuator assembly is configured to releasably engage the trigger and to translate the trigger upstream. A reset mechanism is configured to releasably engage the striker rod and to move the striker rod from the downstream position to the upstream position. A method of operating the impact fatigue device is also disclosed.

18 Claims, 10 Drawing Sheets

(56) References Cited

U.S. PATENT DOCUMENTS

| | | | |
|---|---|---|---|
| 3,879,982 A | 4/1975 | Schmidt | |
| 4,019,374 A | 4/1977 | Tierney et al. | |
| 4,499,906 A | 2/1985 | Wohlgemuth et al. | |
| 5,824,880 A | 10/1998 | Burwell et al. | |
| 6,523,391 B1 | 2/2003 | Knox et al. | |
| 6,742,381 B2 | 6/2004 | Maeno | |
| 6,941,793 B2 * | 9/2005 | Rioux | G01V 1/16 73/12.11 |
| 7,073,405 B2 | 7/2006 | Rioux | |
| 7,380,443 B2 | 6/2008 | Tsujii et al. | |
| 7,412,870 B2 * | 8/2008 | Brankov | G01N 3/303 73/12.11 |
| 7,500,378 B2 | 3/2009 | Tsai et al. | |
| 8,402,811 B2 | 3/2013 | Nie et al. | |
| 8,786,143 B2 | 7/2014 | Gosvener | |
| 2010/0300177 A1 * | 12/2010 | Schwarz | G01N 3/307 73/12.05 |
| 2014/0026635 A1 | 1/2014 | Zorn | |
| 2014/0150526 A1 | 6/2014 | Powers et al. | |
| 2014/0217932 A1 | 8/2014 | Bright et al. | |

\* cited by examiner

N = 220, 4x Magnification

N = 2500, 4x Magnification

DYNAMIC IMPACT FATIGUE DEVICE

CROSS-REFERENCE TO RELATED APPLICATION

The present application claims priority from U.S. Provisional Patent Application 62/142,500, filed on Apr. 3, 2015, which is incorporated herein by reference in its entirety.

BACKGROUND OF THE INVENTION

Impact testing is used to determine the strength of an object or a material over a range of a single impact blow to numerous successive blows. Current commercially available impact machines must be manually reset after each impact or provide only a predetermined, unalterable impact value.

It would be beneficial to provide a dynamic impact fatigue device that can be easily modified either electronically and/or mechanically to deliver a desired rate and/or strength of impact or successive impacts, based on specific testing requirements.

BRIEF SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is an impact fatigue device that includes a striker rod assembly configured to reciprocally move between an upstream position and a downstream position. The striker rod assembly includes a striker rod slidingly mounted on a support member and a trigger located upstream of the striker rod and adapted to move downstream to engage the striker rod and propel the striker rod downstream. An actuator assembly is located upstream of the striker rod assembly. The actuator assembly is configured to releasably engage the trigger and to translate the trigger upstream. A reset mechanism is configured to releasably engage the striker rod and to move the striker rod from the downstream position to the upstream position.

The present invention is also an impact fatigue device that includes a striker rod assembly. The striker rod assembly includes a striker rod movable along a first axis, a bearing assembly slidably supporting the striker rod, and a trigger assembly movable along the first axis between a striker rod disengaged position and a striker rod engaged position. The trigger assembly comprises a striker plate adapted to releasably engage the striker rod, a rear plate coupled to the striker plate, and a biasing member adapted to move the striker plate from an upstream position to a downstream position. An actuator assembly is located upstream of the striker rod assembly. The actuator assembly comprises a magnetic release releasably engageable with the rear plate and a motor connected to the magnetic release and operable to move magnetic release between a magnetic release upstream position and a magnetic release downstream position. A reset mechanism is movable on a second axis. The reset mechanism comprises a reset rod movable along the second longitudinal axis. The reset rod has an engagement end. A retractor wheel is mounted on the engagement end of the reset rod and engageable with the striker rod to move the striker rod from a striker rod downstream position to a striker rod upstream position.

BRIEF DESCRIPTION OF THE DRAWINGS

The aspects, features, and advantages of the present invention will become more fully apparent from the following detailed description, the appended claims, and the accompanying drawings in which like reference numerals identify similar or identical elements.

DETAILED DESCRIPTION OF THE INVENTION

Figure 2:
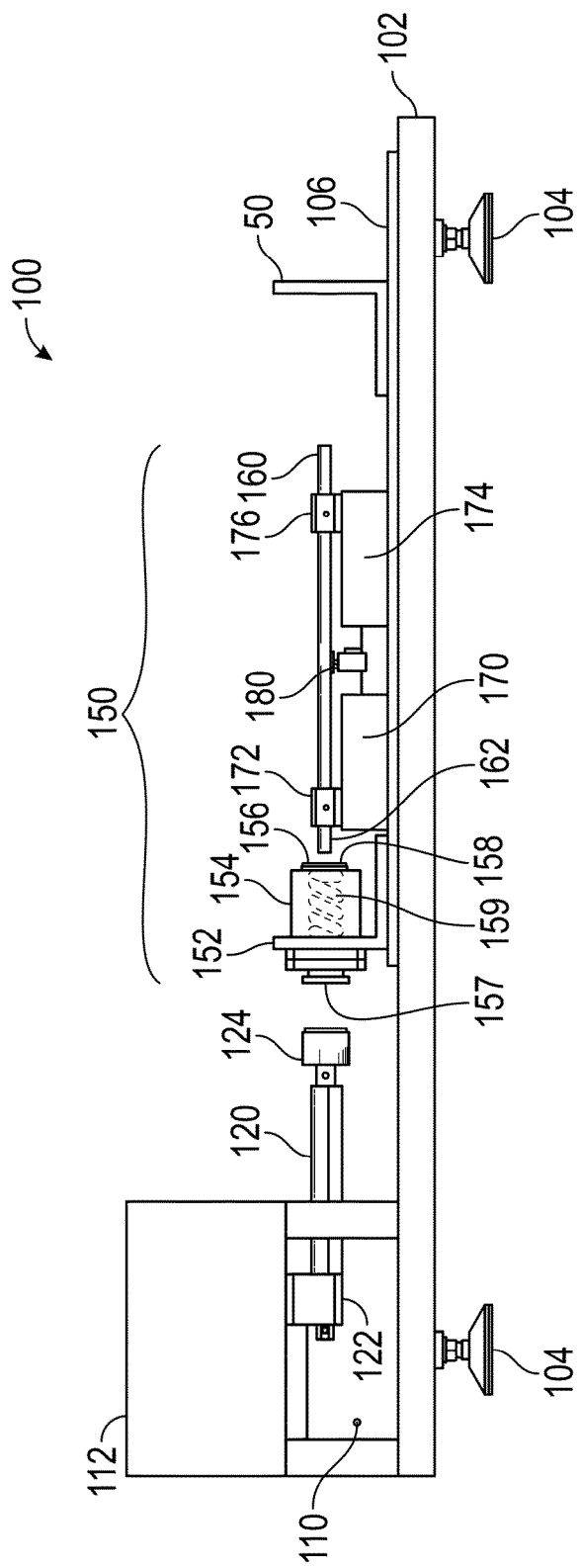
FIG. 2 is a side elevational view of the dynamic impact fatigue device shown in FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "upstream" is defined as a direction toward a power supply in the inventive device, or, to the left as shown in FIG. 2 and the term "downstream" is defined as a direction toward a test specimen in the inventive device, or, to the right as shown in FIG. 2.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

The present invention is a device that is designed to test and characterize repetitive impact loading and determine impact fatigue characteristics of a material or structure. The device uses a spring loaded actuator that fires a projectile, with a separate actuator to automatically reload after each impact. The device also provides the ability to change out both the spring and the projectile to reach a wider range of loading impulses (duration and/or force), and is all fully automated using magnets and actuators. The device has a steel frame to avoid compliance (movement which affects the testing), and has an arrayed screw pattern downrange of the projectile with a large region to house any material in whatever specific orientation to test needed. The device allows for different types of impact testing, whether just striking a target perpendicularly, or conducting more traditional fatigue tests in compression or tension using impact instead of classical load-frame sinusoidal loading. Different rates of impact can be programmed, and even 'random' impact loading can be programmed to simulate a specific event in real-life that has some level of stochasticity in it.

Figure 1:
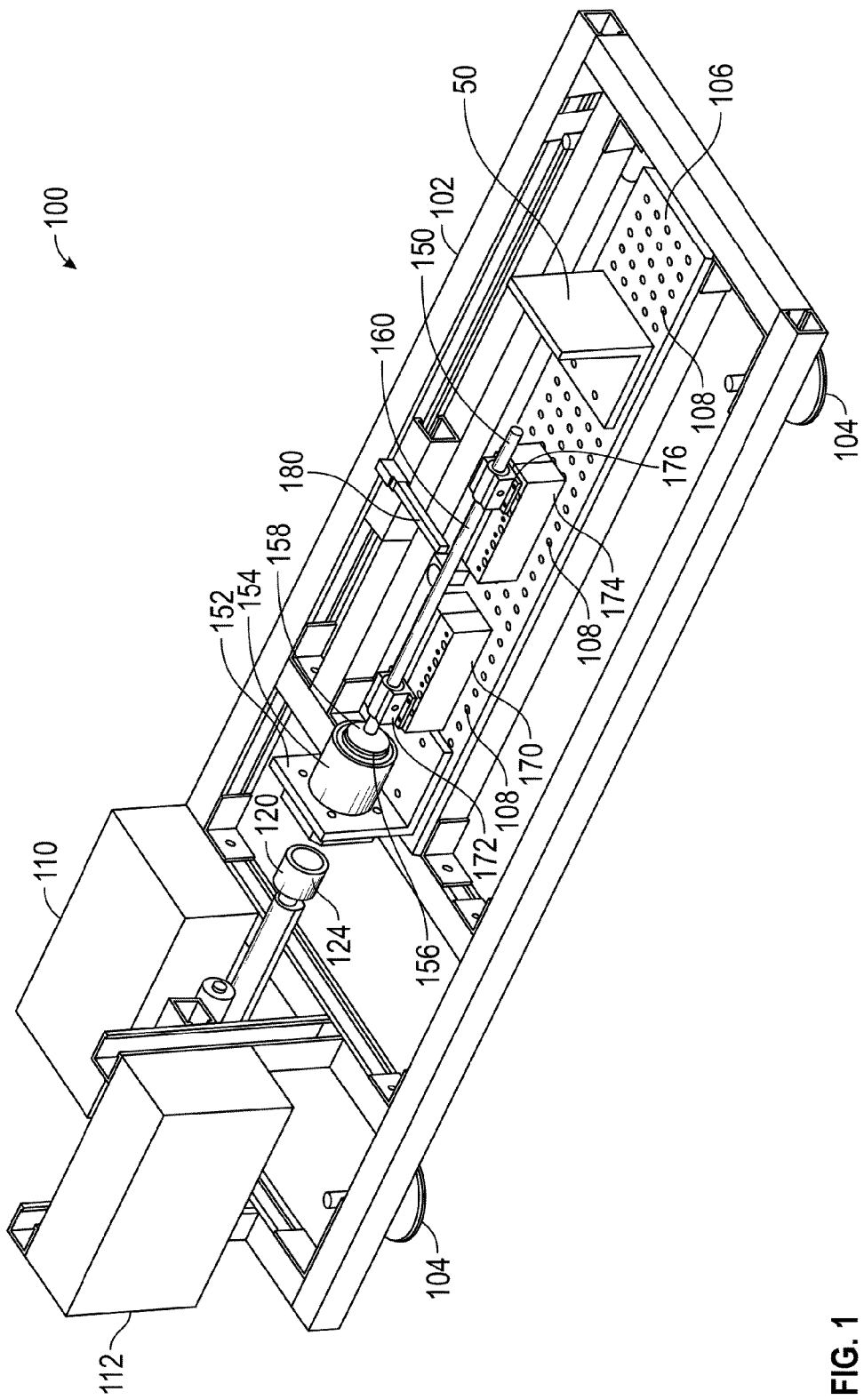
FIG. 1 is a perspective view of a dynamic impact fatigue device according to a first exemplary embodiment of the present invention.
Figure 3:
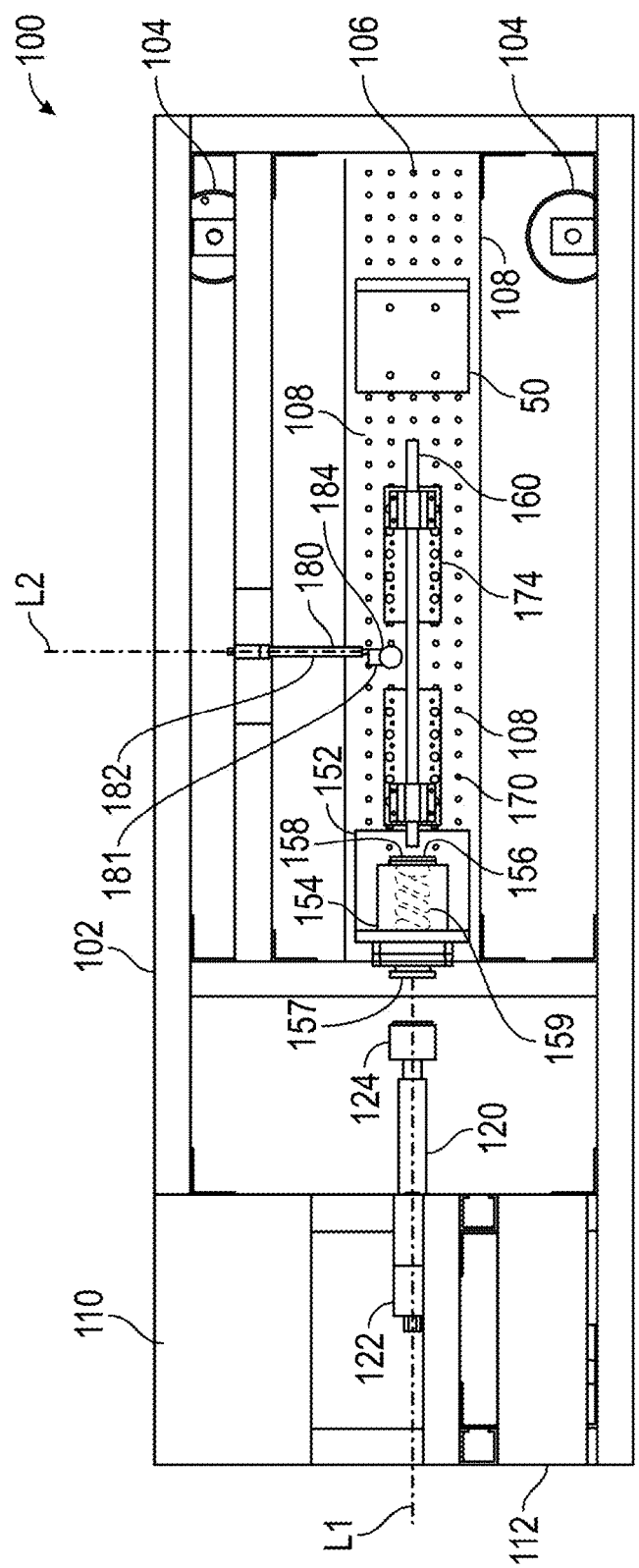
FIG. 3 is a top plan view of the dynamic impact fatigue device shown in FIG. 1.
Figure 4A:
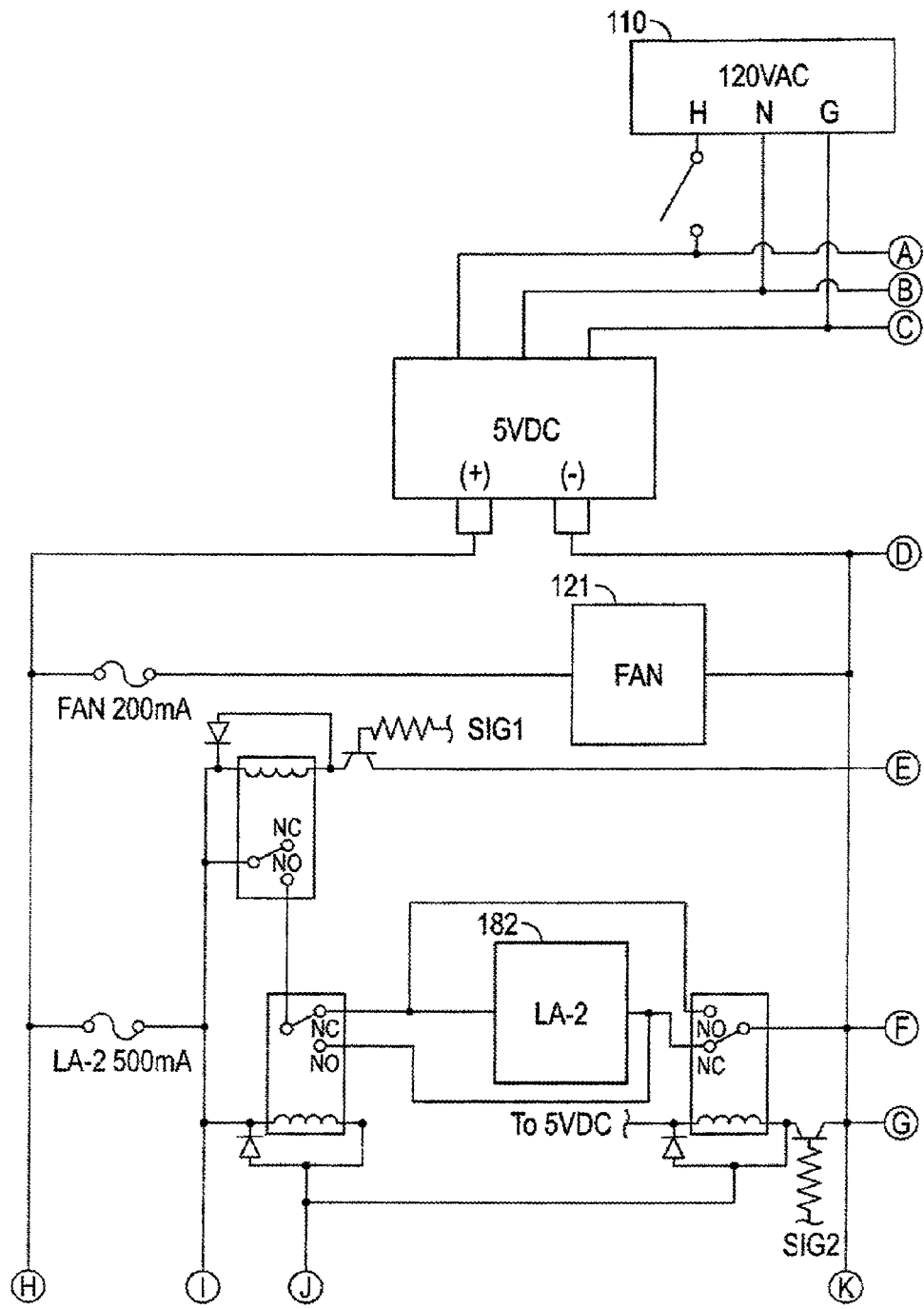
FIGS. 4A-4D is a schematic view of an exemplary embodiment of a control system used with the dynamic impact fatigue device shown in FIG. 1.
Figure 4B:
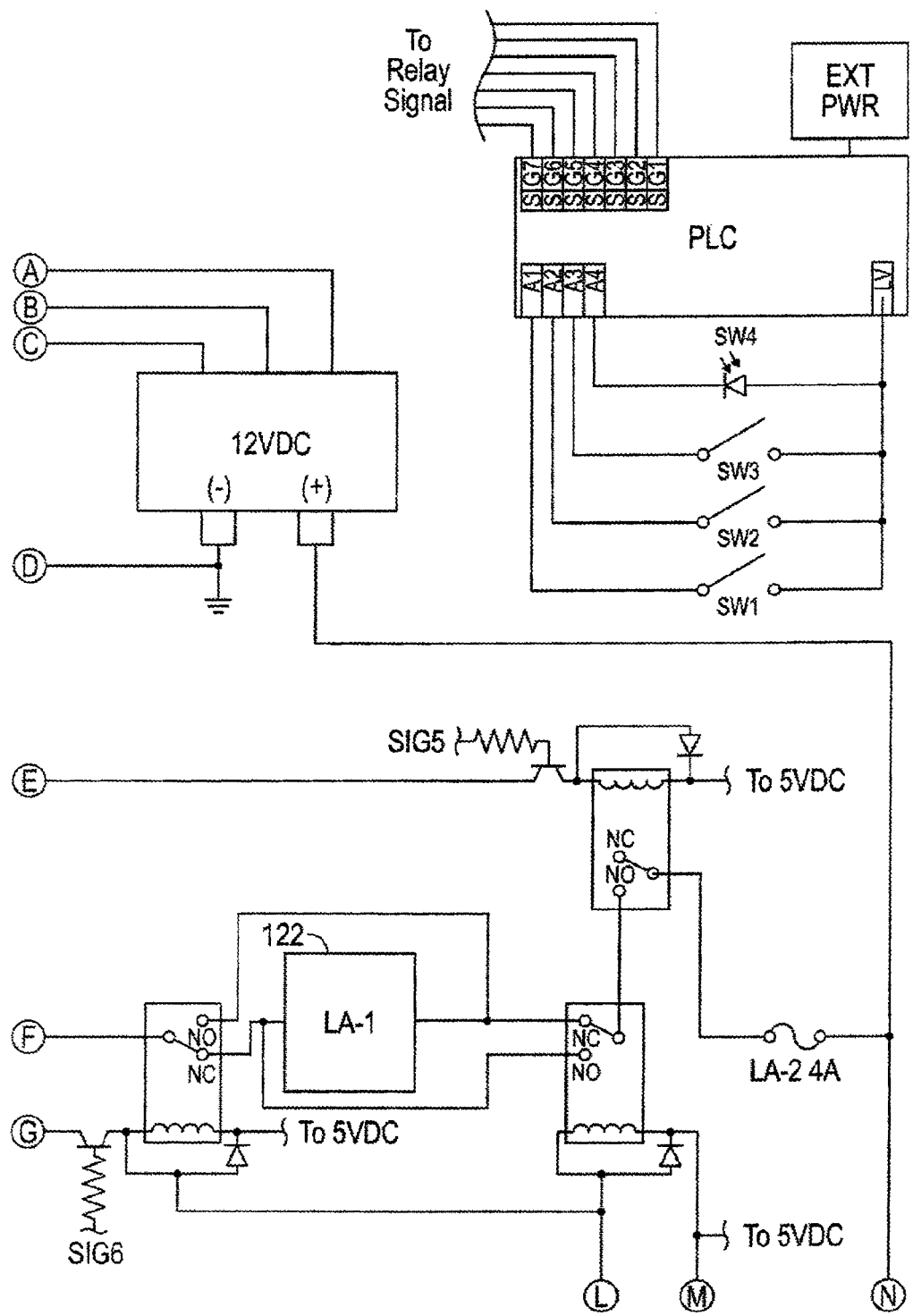
Figure 4C:
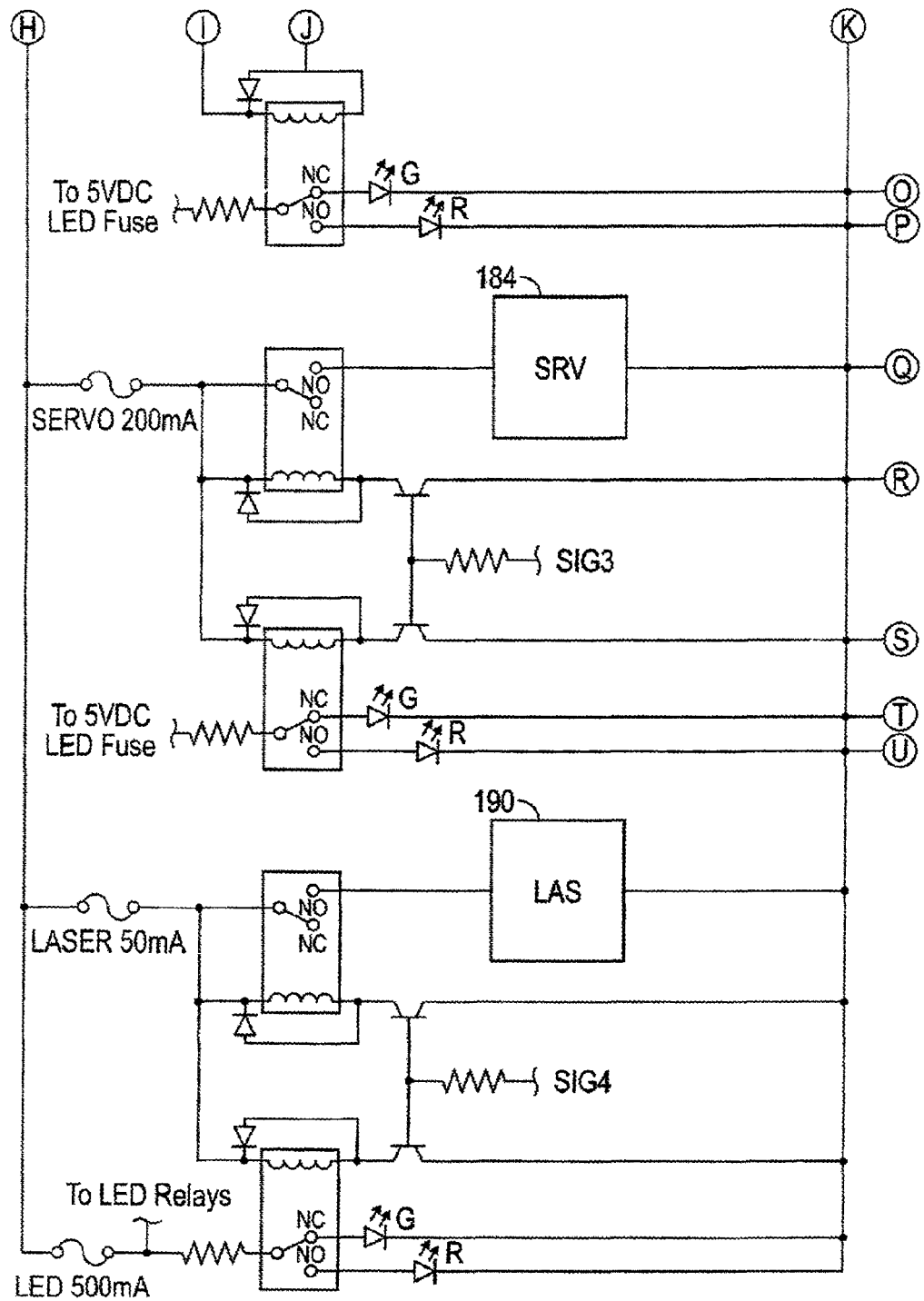
Figure 4D:
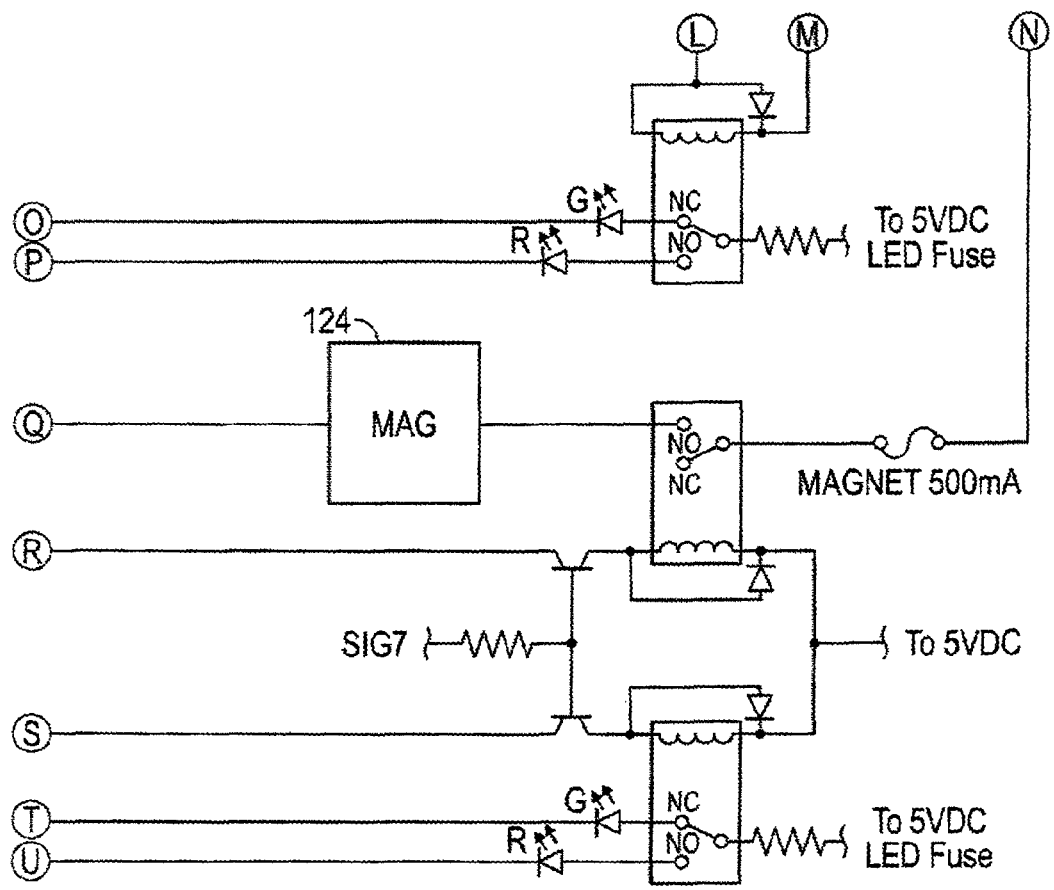

Referring to FIGS. 1-3, a dynamic impact fatigue device 100 ("device 100") according to a first exemplary embodiment of the present invention is shown. Device 100 is used to provide cyclic dynamic impact to a test specimen to test and characterize repetitive impact loading in order to determine impact fatigue characteristics of the specimen. Device 100 provides the ability to simulate different types of impacts. By way of example only, testing performed with device 100 can simulate impacts from running in order to generate microcracks in bone structure, or simulate waves slamming onto a ship's hull.

Device 100 includes a magnetically operated actuator 120 that activates a striker rod assembly 150 for impacting a test specimen 50. After each impact, a reset mechanism 180 returns striker rod assembly 150 to a reset position for a subsequent impact event.

Actuator 120, striker rod assembly 150, reset mechanism 180, and test specimen 50 are mounted on an elongate frame 102 that supports the components of device 100. Frame 102 can be constructed from steel box channel in order to reduce compliance that may adversely affect test results. In an exemplary embodiment, frame 102 can extend between about 36 inches and about 48 inches in length, and between about 10 inches and about 15 inches in width, allowing frame 102 to be mounted on a tabletop (not shown) for ease of use of device 100. Support feet 104 can be located at each corner of frame 102 and can be used to level frame 102 in a known manner.

Frame 102 also supports a mounting plate 106 onto which striker rod assembly 150, reset mechanism 180, and test specimen 50 are directly mounted. Mounting plate 106 can be a breadboard that includes a plurality of evenly spaced threaded openings 108 that allow for selective installation and optional removal and replacement of striker rod assembly 150, reset mechanism 180, and test specimen 50.

Device 100 is operated by a power supply 110 that provides electrical power, such as, for example, from a 110 V alternating current ("AC") electrical outlet. Power supply 110 also includes a converter that converts and lowers the AC voltage to a lower direct current ("DC") voltage, such as, for example, 12 V and/or 5 V (as shown in FIGS. 4A-4D) in order to operate various controllers (not shown—housed in an indication panel 112) on device 100. The controllers can be microprocessors that electronically control operation of various components of device 100, such as, for example, actuator 120 and reset mechanism 180.

Device 100 can be programmed by a remote device (not shown) for multiple operations. Exemplary software to operate device 100 can be MATLAB code. Different rates of impact can be programmed, as well as random impact loading, to simulate specific events in real life that have at least some level of stochasticity. While not shown, other measurement devices can be installed on device 100, with data readouts transmitted to the remote device. Such measurement devices can include, but are not limited to, laser displacement gauges, cameras, and strain gauge electronics.

Indication panel 112 is mounted on frame 102 and provides indicator lights (not shown) to indicate the operational status of device 100. Additionally, power supply 110 can be mounted inside panel 112. In an exemplary embodiment, 17 lights are provided. Three lights indicate system power (Main power, running, and cycle complete). Each of magnetic release 124, retractor wheel 184, and a laser 190 (shown in the schematic of FIGS. 4A-4D) has a pair of LED lights (amber=ON, green=Standby); the remaining 8 lights are used for the two linear motors 120, 182. Each of otors 120, 182 uses 4 lights, (Forward-Standby, Forward-ON, Rev-Standby, Rev-ON). Additionally, indication panel 112 also houses fuses (not shown) that will blow if excessive current is applied. Optionally, a fan 121 (shown in the schematic of FIGS. 4A-4D) can be mounted inside panel 112 to provide cooling to power supply 110.

Actuator 120 includes a linear motor 122 electrically coupled to the controller and activates a magnetic release 124. Linear motor 122 is operated to move magnetic release 124 toward striker rod assembly 150 in order to engage and retract striker rod assembly 150. Magnetic release 124 is an electromagnet such that magnetic release 124 can be electrically actuated to engage striker rod assembly 150. Linear motor 122 is then operated to retract striker rod assembly 150 to a pre-impact position (to the left as shown in FIGS. 2 and 3) to set striker rod assembly 150 for impact. Magnetic release 124 is then deactivated to release striker rod assembly 150 for an impact event.

Striker rod assembly 150 includes a trigger bracket 152 mounted to mounting plate 106. Trigger bracket 152 retains a spring housing 154. Spring housing 154 includes a trigger 156 that provides the energy to drive a striker rod 160. Trigger 156 includes a magnetic rear plate 157 that is engaged by magnetic release 124 to pull rear plate 157 upstream to prepare for an impact event. If desired, the operator can adjust the distance that magnetic release 124 pulls rear plate 157 upstream. For example, rear plate 157 can be pulled upstream only a partial amount in order to reduce the amount of force applied to striker rod 160 and, subsequently, on target specimen 50. Additionally, trigger 156 includes a striker plate 158 that is fixedly connected to rear plate 157, such that, when rear plate 157 is pull upstream by magnetic release 124, striker plate 158 also moves upstream. Striker plate 158 engages a rear end 162 of striker rod 160 to propel striker rod 160 downstream during an impact event. Trigger 156 is mounted in trigger bracket 152 such that, as rear plate 157 is pulled upstream, striker plate 158 compresses trigger 156, storing energy in trigger 156.

In an exemplary embodiment, trigger 156 includes a biasing member, such as a helical spring 159, having defined spring characteristics. Spring 159 is removable from spring housing 154 and replaceable with an alternative spring with differing spring characteristics (i.e., different spring constant value) in order to change operating characteristics of striker rod 160, as desired by the user.

Striker rod 160 is supported on mounting plate 106 by an upstream bearing assembly 170 having a first linear bearing 172 and a downstream bearing assembly 174 having a second linear bearing 176. Bearing assemblies 170, 174 are releasably mounted to mounting plate 106 and are adjustable as desired.

Figure 5:
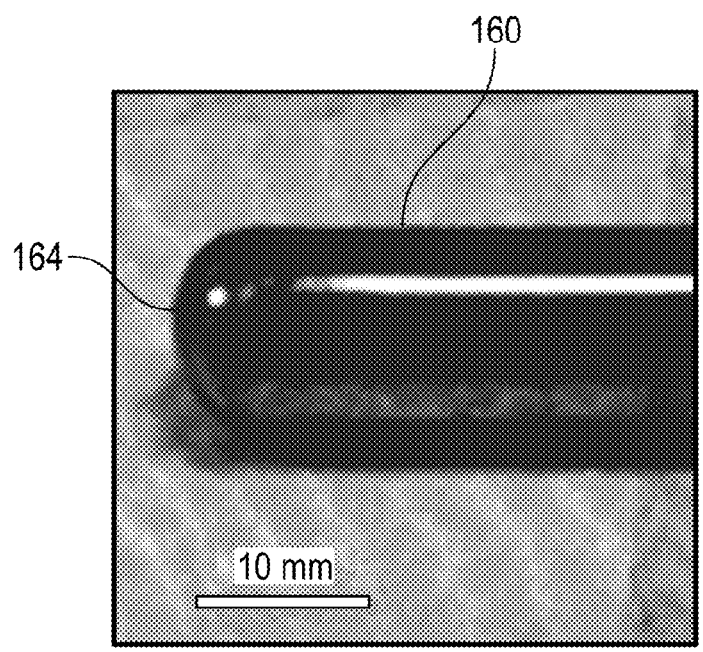
FIG. 5 is an enlarged view of a distal tip of an exemplary striker rod used in the dynamic impact fatigue device shown in FIG. 1.

Striker rod 160 is an elongate, generally cylindrical rod that is slidingly mounted in first linear bearing 172 and second linear bearing 176 for movement along a linear axis L1 in a downstream/upstream direction. Striker rod 160 includes a downstream tip 164 that is used to impact test specimen 50. Downstream tip 164 of an exemplary striker rod 160 is shown in FIG. 5. While the tip 164 shown in FIG. 5 is generally rounded, other striker rod (not shown) can be used with different tips, such as, for example, a blunt tip, a sharp tip, or other shapes of tips. Also, while striker rod 160 shown in FIG. 5 instructed from a metallic material, those skilled in the art will recognize that striker rod 160 can be constructed from other materials and dimensions to impart a different loading profile onto test specimen 50 as well.

Operationally, biasing member 159 and striker rod 160 are each selected based on the type of testing that is to be conducted and actuator assembly 120 is programmed to adjust the distance that magnetic release 124 translates rear plate 157 upstream. A target 50 is located downstream of striker rod 160 and is secured to mounting plate 106. When all indicator lights and other indicia indicate that system 100 is ready for operation, magnetic release 124 is translated downstream to engage rear plate 157 by electronically operating linear motor 122. The electromagnet on magnetic release 124 is electronically activated to magnetically secure magnetic release 124 to rear plate 157 and linear motor 122. Magnetic release 24 and rear plate 157 (with attached striker plate 158) are translated upstream by electronically operating linear motor 122, compressing biasing member 159. The electromagnet on magnetic release 124 is electronically deactivated to release rear plate 157. Biasing member 159 expands, translating striker plate 158 downstream where striker plate 158 strikes striker rod 160, which in turn strikes specimen 50.

After striker rod 160 strikes test specimen 50, magnetic release 124 and reset mechanism 180 are used to reset striker rod 160 for a subsequent impact event. Linear motor 122 electronically drives magnetic release 124 downstream to magnetically re-engage rear plate 157 and then reverses direction to electronically pull magnetic release 124 upstream, pulling striker plate 158 upstream and compressing biasing member 159.

As striker plate 158 is being pulled upstream, reset mechanism 180 is electronically operated to engage striker rod 160 to slide striker rod 160 upstream. Reset mechanism 180 includes a linear motor 182 that is set along a linear axis L2 generally perpendicular to linear axis L1 of striker rod 160. A motorized retractor wheel 184 is mounted on an engagement end 181 of linear motor 182 proximate to striker rod 160. Linear motor 182 is electronically operated to extend retractor wheel 184 until retractor wheel 184 engages striker rod 160. Retractor wheel 184 is then electronically operated to rotate and frictionally slide striker rod 160 upstream until striker rod 160 is reset for the next impact event.

After striker rod 160 is reset, retractor wheel 184 stops rotating and linear motor 182 is electronically operated to reverse direction to retract retractor wheel 184 away from striker rod 160. Device 100 is now ready for the next impact event.

Optionally, a laser 190 works in conjunction with a photoreceptor (not shown) to detect when the laser beam has been broken. In a typical arrangement, the laser beam would cross over the path of striker rod 160, allowing the user to trigger external electronics (high-speed cameras, flash bulbs, etc.) when striker rod 160 breaks the beam in mid-flight. Laser 190 has no set location. Because mounting plate 106 is a breadboard, the user can locate laser 190 in any position to capture their event using typical optical breadboard mounting systems known in the art (Thor Labs, Edmunds, etc.). For instance, using the above example, a shorter striker rod 160 would require laser 190 to be located closer to the actuator 120, whereas a longer striker rod 160 will have laser 190 positioned closer to the downstream end of device 100.

Figure 6:
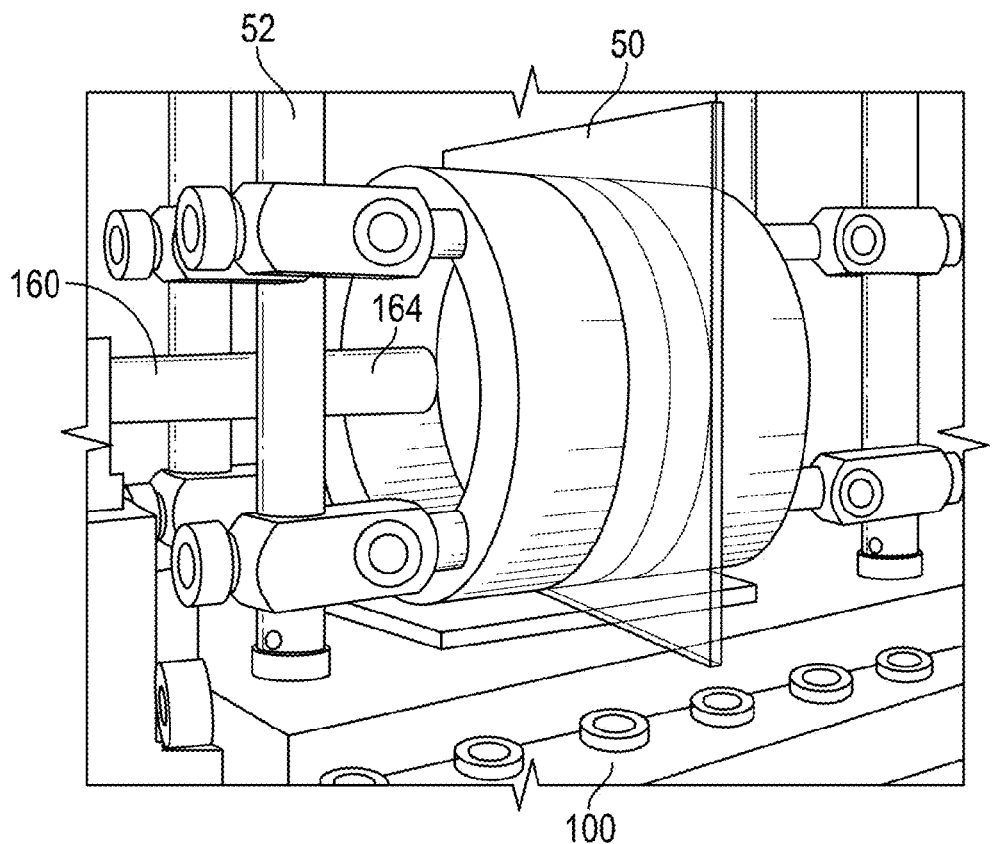
FIG. 6 is a perspective view of a test specimen installed in the dynamic impact fatigue device shown in FIG. 1.

Referring now FIG. 6, an exemplary test specimen 50 is shown. Test specimen 50 is a polycarbonate material having dimensions of 100 mm×100 mm with a thickness of about 2.38 mm. Test specimen 50 is supported on device 100 by a removable support 52 that vertically supports test specimen 50 while allowing striker rod 160 to impact test specimen 50. Support 152 is secured to device 100 via mounting plate 106. As shown in FIG. 6, striker rod 160 has a generally blunt tip 164, and not the generally rounded tip shown in FIG. 5.

While test specimen 50 is shown as extending in a plane generally perpendicular to the axis of movement of striker rod 160, those skilled in the art will recognize that test specimen 50 can be rotated relative to the axis of movement of striker rod 160, resulting in glancing blows rather than the direct, straight-on impact provided by the configuration shown in FIG. 5. Additionally, different support structures (not shown) can be provided and mounted onto mounting plate 106 to test a single crack impact fatigue in Mode I (crack opening), Mode II (crack sharing), Mode III (crack tearing), and/or mixed mode and random impact capability.

Figure 7:
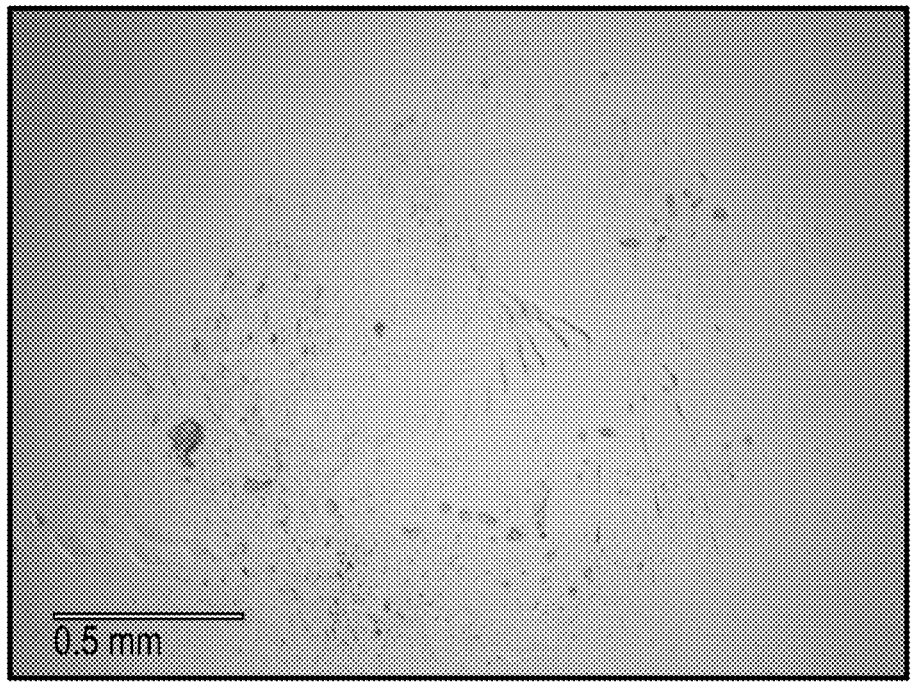
FIG. 7 is a 4× magnified photograph showing damage to a first test specimen after 220 impacts using the dynamic impact fatigue device shown in FIG. 1.
Figure 8:
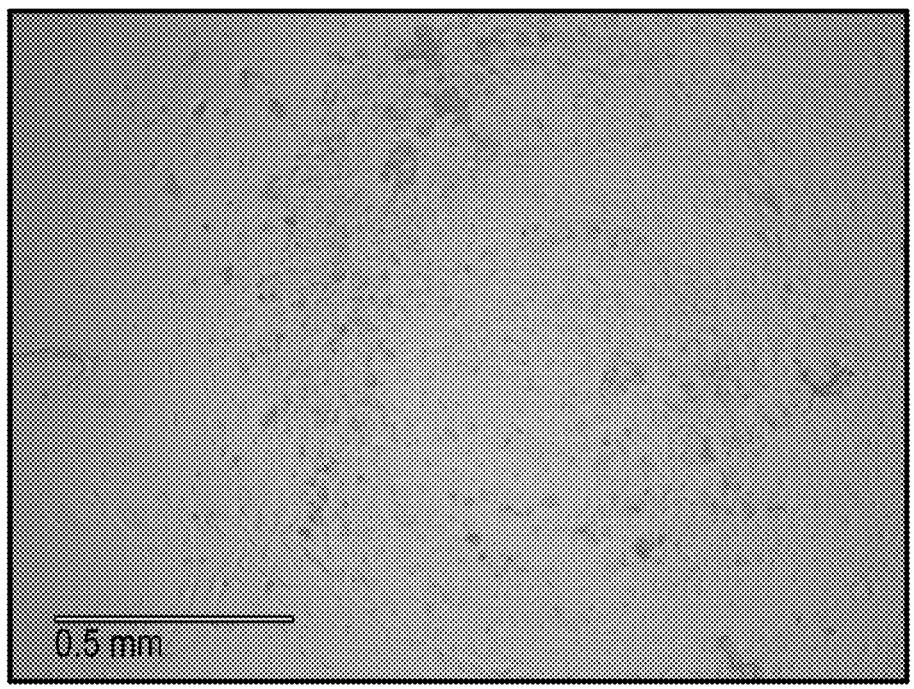
FIG. 8 is a 4× magnified photograph showing damage to the first test specimen after 2500 impacts using the dynamic impact fatigue device shown in FIG. 1.

FIG. 7 is a 4× magnified photograph showing damage to a test specimen 50 with a striker rod 160 having a rounded tip 164, having been impacted with 220 impacts. The tip of striker rod 160 was ground to a radius slightly larger than striker rod 160. For a 12.7 mm rod (½ inch), the radius of the tip is 7.94 mm (per ASTM D5628-10). Striker rod 160 is made from a hardened steel shaft (Rockwell C60 hardness), while specimen 50 was polycarbonate. The impact energy is about 0.15 J with striker rod 160 having a velocity of about 1 m/s. FIG. 8 is a 4× magnified photograph of the same specimen after 2500 impacts under the same striking conditions. A comparison of FIG. 8 with FIG. 7 shows the difference in the condition of specimen 50 over the additional number of impacts.

Figure 9:
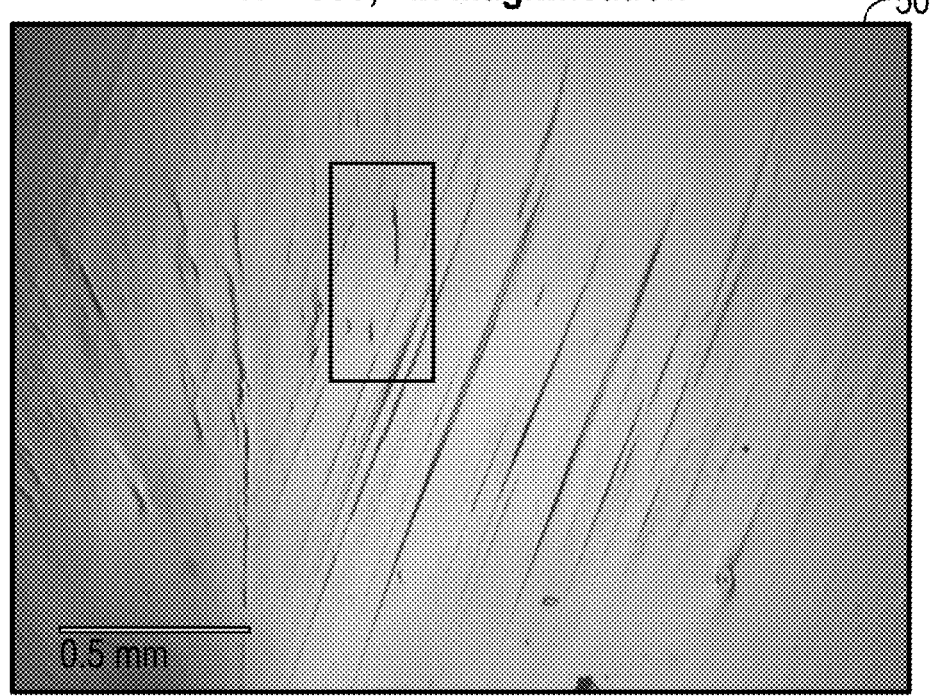
FIG. 9 is a 4× magnified photograph showing damage to a second test specimen after 500 impacts using the dynamic impact fatigue device shown in FIG. 1.
Figure 10:
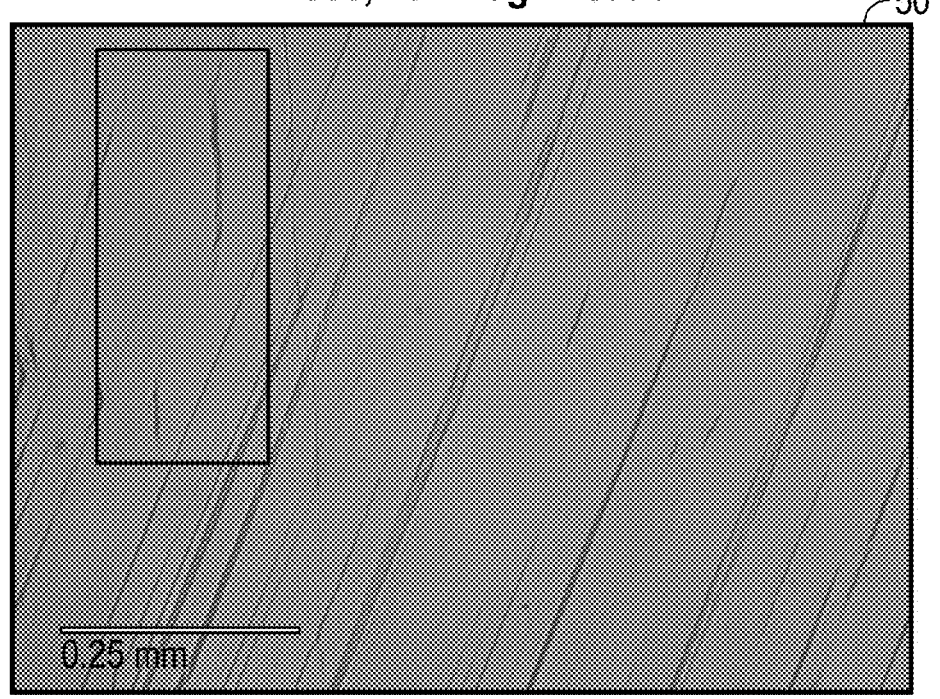
FIG. 10 is a 10× magnified photograph showing damage to the second test specimen after 500 impacts using the dynamic impact fatigue device shown in FIG. 1.

FIG. 9 is a 4× magnified photograph showing damage to a test specimen 50' with striker rod 160, having been impacted with 220 impacts. The impact energy is about 0.6 J, with striker rod 160 having a velocity of about 2 m/s. FIG. 10 is a 10× magnified photograph of the specimen shown in FIG. 9.

In comparing the impact energy and speed of specimen 50, shown in FIGS. 7 and 8, with the impact energy and speed of specimen 50', shown in FIGS. 9 and 10, one can see a higher energy and speed with respect to specimen 50'. The higher energy and speed can be a function of replacing spring 159 with a replacement spring having a higher spring constant and/or replacing striker rod 160, with a replacement striker rod with a different mass and/or material.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. An impact fatigue device comprising:
   (a) a striker rod assembly configured to reciprocally move between an upstream position and a downstream position, the striker rod assembly comprising:
      i. a striker rod slidingly mounted on a support member; and
      ii. a trigger located upstream of the striker rod and adapted to move downstream to engage the striker rod and propel the striker rod downstream;
   (b) an actuator assembly located upstream of the striker rod assembly, the actuator assembly configured to releasably engage the trigger and to translate the trigger upstream; and
   (c) a reset mechanism configured to releasably engage the striker rod and to move the striker rod from the downstream position to the upstream position,
   wherein the striker rod assembly and the actuator assembly are operable along a first longitudinal axis and wherein the reset mechanism is operable along a second longitudinal axis, perpendicular to the first longitudinal axis,
   wherein the reset mechanism comprises:
      (a) a reset rod movable along the second longitudinal axis, the reset rod having an engagement end; and
      (b) a retractor wheel mounted on the engagement end of the reset rod and engageable with the striker rod to move the striker rod from the downstream position to the upstream position, wherein the reset rod moves the retractor wheel linearly.

2. The impact fatigue device according to claim 1, wherein the actuator assembly comprises an electromagnet releasably engageable with the trigger such that, when the electromagnet is activated, the actuator assembly engages the trigger and, when the electromagnet is deactivated, the actuator assembly releases the trigger.

3. The impact fatigue device according to claim 2, wherein the actuator assembly further comprises a motor configured to move the electromagnet between a downstream position wherein the electromagnet engages trigger and a downstream position wherein the electromagnet releases the trigger.

4. The impact fatigue device according to claim 1, wherein the support member comprises a first bearing located at an upstream end of the striker rod and a second bearing located at a downstream end of the striker rod.

5. The impact fatigue device according to claim 1, further comprising a biasing member adapted to move the trigger from an upstream position wherein the trigger is out of engagement with the striker rod and a downstream position wherein the trigger engages the striker rod.

6. The impact fatigue device according to claim 5, wherein the biasing member, and the trigger are supported within a spring housing, and wherein the biasing member is removably insertable into the spring housing.

7. The impact fatigue device according to claim 1, further comprising a mounting plate located downstream of the striker Rod, the mounting plate adapted to releasably secure a test specimen.

8. A method of operating an impact fatigue device, comprising the steps of:
   (a) providing the impact fatigue device according to claim 1;
   (b) placing a test specimen downstream of the striker rod;
   (c) activating the actuator assembly to releasably engage the trigger;
   (d) operating the actuator assembly to translate the trigger upstream;
   (e) deactivating the actuator assembly to release the trigger;
   (f) impacting the striker rod with the trigger;
   (g) propelling the striker rod downstream; and
   (h) impacting a test specimen with the striker rod.

9. The method according to claim 8, further comprising, after step (h), the steps of:
   (i) engaging the striker rod with the reset mechanism;
   (j) using the reset mechanism to translate the striker rod upstream; and
   (k) repeating steps (a) through (j).

10. The method according to claim 9, wherein step (i) comprises the step of translating the reset mechanism generally perpendicular to the striker rod.

11. The method according to claim 9, wherein steps (c)-(e), (i), and (j) are performed electronically.

12. The method according to claim 8, wherein step (c) comprises the steps of:

translating the actuator assembly downstream; and magnetically engaging the trigger.

13. The method according to claim 8, wherein step (e) comprises the step of magnetically disengaging the trigger.

14. The method according to claim 8, wherein the trigger comprises a first biasing member, and wherein the method comprises, after step (a) and before step (c), removing the first biasing member, and replacing the first biasing member with a second biasing member having different operational characteristics than the first biasing member.

15. An impact fatigue device comprising:
(a) a striker rod assembly comprising:
 i. a striker rod movable along a first axis;
 ii. a bearing assembly slidably supporting the striker rod;
 iii. a trigger assembly movable along the first axis between a striker rod disengaged position and a striker rod engaged position, the trigger assembly comprising:
  1. a striker plate adapted to releasably engage the striker rod;
  2. a rear plate coupled to the striker plate; and
  3. a biasing member adapted to move the striker plate from an upstream position to a downstream position;
(b) an actuator assembly located upstream of the striker rod assembly, the actuator assembly comprising:
 i. a magnetic release releasably engageable with the rear plate; and
 ii. a motor connected to the magnetic release and operable to move magnetic release between a magnetic release upstream position and a magnetic release downstream position; and
(c) a reset mechanism movable on a second axis, the reset mechanism comprising:
 i. a reset rod movable along the second longitudinal axis, the reset rod having an engagement end; and
 ii. a retractor wheel mounted on the engagement end of the reset rod and engageable with the striker rod to move the striker rod from a striker rod downstream position to a striker rod upstream position, wherein the reset rod moves the retractor wheel linearly.

16. The impact fatigue device according to claim 15, wherein the biasing member is removable from the trigger assembly.

17. The impact fatigue device according to claim 15, wherein the magnetic release comprises an electromagnet.

18. The impact fatigue device according to claim 15, wherein the second longitudinal axis is generally perpendicular to the first longitudinal axis.

* * * * *